US012708434B2

(12) United States Patent
Iijima

(10) Patent No.: US 12,708,434 B2
(45) Date of Patent: Aug. 18, 2026

(54) BALLOON CATHETER AND METHOD OF ACTUATING BALLOON CATHETER

(71) Applicant: Japan Lifeline Co., Ltd., Tokyo (JP)

(72) Inventor: Toshiyuki Iijima, Tokyo (JP)

(73) Assignee: Japan Lifeline Co., Ltd., Tokyo (JP)

( * ) Notice: Subject to any disclaimer, the term of this patent is extended or adjusted under 35 U.S.C. 154(b) by 620 days.

(21) Appl. No.: 18/159,440

(22) Filed: Jan. 25, 2023

(65) Prior Publication Data

US 2023/0248425 A1 Aug. 10, 2023

(30) Foreign Application Priority Data

Feb. 8, 2022 (JP) ................................ 2022-017952

(51) Int. Cl.
*A61B 18/14* (2006.01)
*A61B 18/00* (2006.01)

(52) U.S. Cl.
CPC .. *A61B 18/1492* (2013.01); *A61B 2018/0022* (2013.01); *A61B 2018/00577* (2013.01)

(58) Field of Classification Search
CPC ............................................ A61B 2018/0022
See application file for complete search history.

(56) References Cited

U.S. PATENT DOCUMENTS 5,846,238 A * 12/1998 Jackson ................ A61N 1/056 606/41
5,871,483 A * 2/1999 Jackson ............ A61B 18/1492 606/41
8,551,096 B2 * 10/2013 Perry ................ A61B 18/1492 604/382
8,951,251 B2 * 2/2015 Willard ............... A61B 18/082 606/41
2008/0188912 A1 * 8/2008 Stone ....................... A61F 7/12 606/192

(Continued)

FOREIGN PATENT DOCUMENTS

CN 109843201 A 6/2019
CN 112512451 A 3/2021

(Continued)

OTHER PUBLICATIONS

JP Office Action issued for corresponding Japanese Patent Application No. 2022-017952 with Machine Translation.

(Continued)

*Primary Examiner* — Ronald Hupczey, Jr.
(74) *Attorney, Agent, or Firm* — Shih IP Law Group, PLLC

(57) ABSTRACT

The balloon catheter includes a shaft to be inserted into a body, a balloon that is attached to a distal end side of the shaft and expandable by a fluid supplied from a proximal end side of the shaft, and an electrode pair that is formed on a surface of the balloon along an axial direction from the proximal end side toward the distal end side. Widths in a circumferential direction of respective band-shaped electrodes are greater than a width of an electrode clearance that separates the respective band-shaped electrodes in the circumferential direction in the electrode pair. A plurality of the electrode pairs are formed on the surface of the balloon. A width of an electrode pair clearance that separates the respective electrode pairs, in the circumferential direction is greater than the width of the electrode clearance.

8 Claims, 10 Drawing Sheets

(56) References Cited

U.S. PATENT DOCUMENTS

2014/0309579 A1* 10/2014 Rubinsky ................ A61M 5/14
606/41
2015/0141982 A1* 5/2015 Lee ........................ A61B 5/287
606/41
2017/0296266 A1* 10/2017 Salahieh ............ A61B 1/00082
2017/0348049 A1 12/2017 Vrba et al.
2019/0030328 A1* 1/2019 Stewart .............. A61B 18/1492
2021/0361220 A1* 11/2021 Olson .................... A61B 5/287
2022/0104872 A1* 4/2022 Govari ................. A61B 5/6853

FOREIGN PATENT DOCUMENTS

WO WO-9732532 A1 * 9/1997 ......... A61B 18/1492
WO WO2021/157100 8/2021

OTHER PUBLICATIONS

Office Action dated Jan. 21, 2026 issued in corresponding China Application No. 202310065900.3 (with English translation) 12 pages.
Office Action from CN Application No. 202310065900.3 mailed May 9, 2026, 13 pages.

* cited by examiner

BALLOON CATHETER AND METHOD OF ACTUATING BALLOON CATHETER

TECHNICAL FIELD

The present disclosure relates to, for example, a balloon catheter including a balloon that can be expanded in a body.

BACKGROUND ART

A catheter is a medical tube inserted into a body for diagnosis or treatment. In particular, a catheter including a balloon that can be expanded in a body is referred to as a balloon catheter, and is inserted into: for example, a tubular organ in a body, such as blood vessels, trachea, gastrointestinal tract, common bile duct, and pancreatic ductus; a connection part (inlet and outlet) between these; and a hole formed in the body for diagnosis or treatment (a hole that is punctured into the common bile duct from the stomach and the duodenal bulb, for example) for expanding or treating a target site.

As disclosed in Patent Literature 1, a balloon catheter in which band-shaped electrodes where a high-frequency wave (hereinafter abbreviated and also referred to as a high frequency) is applied are formed on a surface of a balloon is used for catheter ablation (hereinafter abbreviated and also referred to as ablation) or Radiofrequency Ablation (RFA), which are treatment methods for, for example, an arrhythmia. The balloon inserted up to an abnormal site (a surrounding tissue, such as a vessel itself or a focus) in a vessel, such as a blood vessel, responsible for an arrhythmia expands by an expansion fluid, such as saline, supplied therein, bringing the electrodes on the surface close to or in contact with the abnormal site. The abnormal site is ablated by the high frequency applied to the electrodes in this state.

CITATION LIST

Patent Document

Patent Literature 1: WO 2021/157100

SUMMARY OF INVENTION

Technical Problem

Although the balloon prior to expansion is folded, when a fold is formed on the electrodes on the surface of the balloon, a change in a conduction aspect of the high frequency on the electrodes possibly failed to perform a stable treatment.

The present disclosure has been made in view of such circumstances, and an object thereof is to provide, for example, a balloon catheter that can prevent an unstable treatment due to folding of a balloon.

Solution to Problem

To solve the problem described above, a balloon catheter according to an aspect of the present disclosure includes a shaft, a balloon, and an electrode pair. The shaft is to be inserted into a body. The balloon is attached to a distal end side of the shaft and expandable by a fluid supplied from a proximal end side of the shaft. The electrode pair is formed on a surface of the balloon along an axial direction from the proximal end side toward the distal end side. Widths in a circumferential direction of respective electrodes are greater than a width of an electrode clearance that separates the respective electrodes in the circumferential direction in the electrode pair. A plurality of the electrode pairs are formed on the surface of the balloon. A width of an electrode pair clearance that separates the respective electrode pairs in the circumferential direction is greater than the width of the electrode clearance.

In this aspect, since foldability of the balloon is improved by the electrode clearance in each of the electrode pairs and the electrode pair clearance between the respective electrode pairs, a possibility of formation of a fold of the balloon on the electrodes decreases.

Another aspect of the present disclosure is a method of actuating a balloon catheter. The method includes expanding a balloon attached to a distal end side of a shaft and folded such that a fold is not formed on a plurality of electrodes formed along an axial direction from a proximal end side toward the distal end side on a surface of the balloon by a fluid.

Advantageous Effects of Invention

For example, the balloon catheter of the present disclosure allows preventing an unstable treatment due to folding of the balloon.

DESCRIPTION OF EMBODIMENTS

Figure 1:
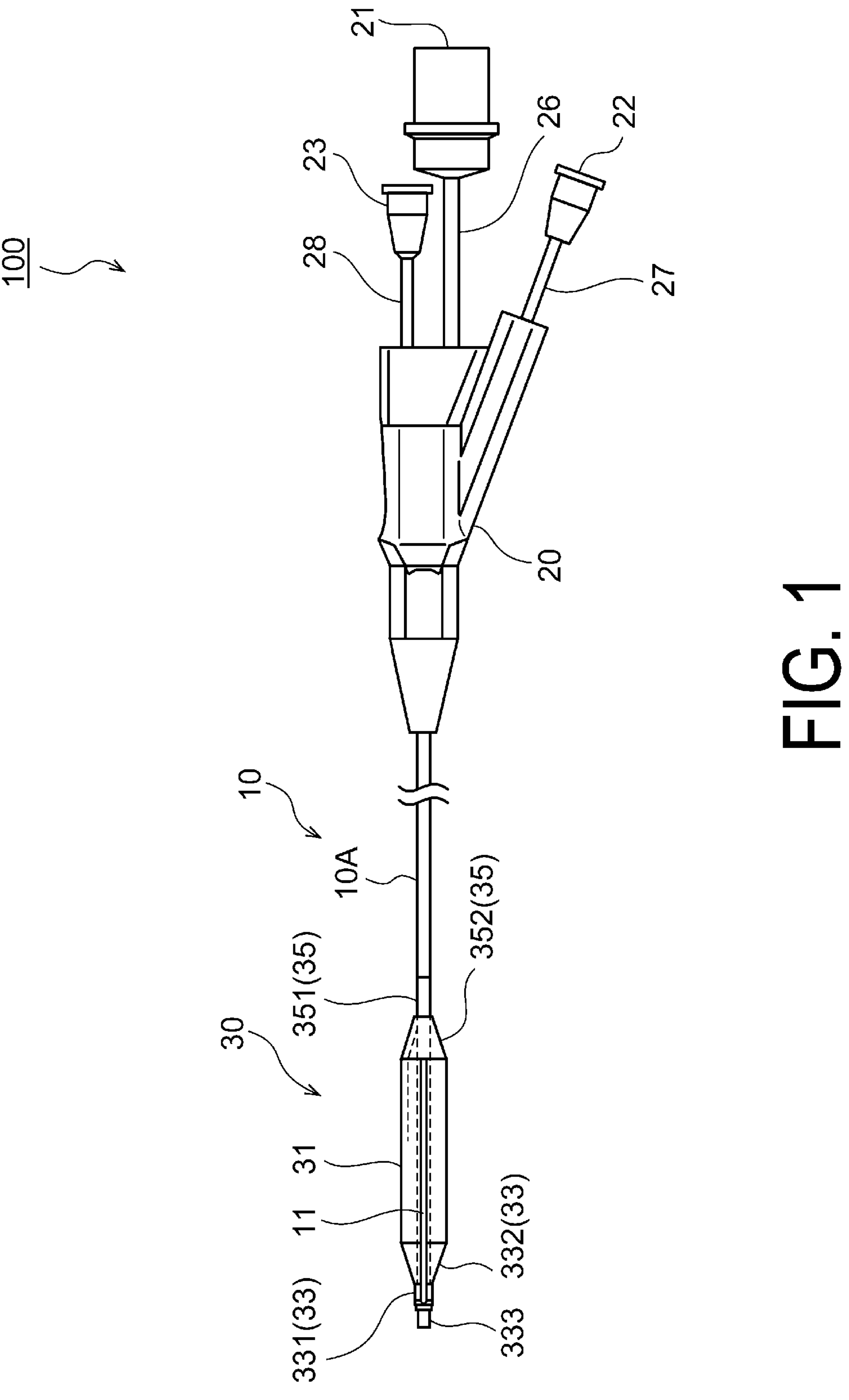
FIG. 1 illustrates an entire balloon catheter.

Hereinafter, embodiments for carrying out the present disclosure will be described in detail with reference to the drawings. In the description or drawings, the same or equivalent constituent elements, members, and processing operations are denoted by the same reference numerals, and overlapping descriptions are omitted. The scales and shapes of the illustrated parts are set for convenience to facilitate the explanation and should not be construed as limiting unless otherwise specified. The embodiments are illustrative and do not limit the scope of the present disclosure in any way. Not all features or combinations of features described in the embodiments are essential to the present invention.

FIG. 1 illustrates an entire balloon catheter 100 according to an embodiment of the present embodiment. The balloon catheter 100 includes a flexible tubular shaft 10 to be inserted into a body, a handle portion 20 attached to a proximal end side or a side outside the body (the right side in FIG. 1) of the shaft 10, and a balloon 30 that is attached to a distal end side or a side inside the body (the left side in FIG. 1) of the shaft 10 and can expand by a fluid supplied from the proximal end side of the shaft 10. The shaft 10 includes a tubular outer tube 10A that extends from the handle portion 20 to a proximal end portion (a proximal end side neck portion 351 described later) of the balloon 30, a tubular inner shaft 11 that communicates with the outer tube 10A and penetrates the inside of the balloon 30 in an axial direction (the right-left direction in FIG. 1), and a distal end tip 333 attached to the distal end portion of the inner shaft 11.

The balloon catheter 100 is used for ablation for ablating a focus. As described later, a band-shaped electrode group is formed on the surface of the balloon 30 along the axial direction from the proximal end side toward the distal end side. The balloon 30 inserted up to an abnormal site in a vessel, such as a blood vessel, expands by an expansion fluid, such as saline, supplied therein via the handle portion 20 and the shaft 10, bringing the electrode group on the surface close to or in contact with the abnormal site. The electrode group to which a high frequency is applied ablates the abnormal site in this state.

To the proximal end side of the handle portion 20, an electrical connector 21, a fluid supply/discharge port 22, and a guidewire port 23 are connected. The electrical connector 21 is electrically connected to the electrode group on the surface of the balloon 30 by a conductive wire passing through an electrical cable 26, the handle portion 20, the shaft 10 (the outer tube 10A and/or the inner shaft 11), and the inside of the balloon 30 from the proximal end side toward the distal end side. Thus, the electrical connector 21 connected to a high-frequency power supply (not illustrated) can apply a high frequency to the electrode group on the surface of the balloon 30. Also, by connecting the electrical connector 21 to a control device or a measurement device constituted by, for example, a computer, data of, for example, a potential at a treatment site measured by the electrode group on the surface of the balloon 30 may be acquired.

The fluid supply/discharge port 22 supplies and discharges a fluid to expand the balloon 30, specifically an expansion fluid produced by appropriately mixing a contrast fluid to sterile distilled water or saline. The fluid supply/discharge port 22 communicates with the inside of the balloon 30 with a flow path passing through the inside of a fluid supply/discharge tube 27, the handle portion 20, and the shaft 10 (the outer tube 10A) from the proximal end side toward the distal end side. When the fluid supply/discharge port 22 supplies the expansion fluid to the inside of the balloon 30, the balloon 30 expands. When the fluid supply/discharge port 22 discharges the expansion fluid from the inside of the balloon 30, the balloon 30 contracts. As disclosed in International Application PCT/JP2020/005007 (International Publication No. 2021/157100) filed on Feb. 8, 2020, the entire contents of which are incorporated herein by reference, a port and a flow path for supplying the expansion fluid to the inside of the balloon 30 and a port and a flow path for discharging the expansion fluid from the inside of the balloon 30 may be individually provided.

Into the guidewire port 23, a guidewire to guide the balloon 30 to the treatment site is inserted. From the guidewire port 23, a hole (space) passing through a wire tube 28, the handle portion 20, the shaft 10 (the outer tube 10A and the inner shaft 11), and the inside of the balloon 30 penetrates up to the distal end portion of the balloon catheter 100, from the proximal end side toward the distal end side. Insertion of the distal end portion of the balloon catheter 100 from the proximal end portion of the guidewire inserted up to the treatment site in advance allows the balloon 30 to reach the treatment site while being guided by the guidewire.

A fluid lumen and a wire lumen are provided inside the tubular shaft 10, in addition to the conductive wire that electrically conducts the electrical connector 21 and the electrode group on the surface of the and the balloon 30. The fluid lumen is a space where the expansion fluid flows between the fluid supply/discharge port 22 and the inside of the balloon 30. The wire lumen is a space that penetrates between the guidewire port 23 and the distal end portion of the balloon catheter 100. The distal end of the fluid lumen, which is also the distal end of the outer tube 10A, is an open end terminating inside the balloon 30. Also, the distal end of the wire lumen, which is also the distal end of the inner shaft 11, is an open end at the distal end of the balloon catheter 100 itself. In this way, among the outer tube 10A constituting the shaft 10 and the inner shaft 11, while the outer tube 10A forming the fluid lumen terminates inside the balloon 30, the inner shaft 11 forming the wire lumen axially penetrates the inside of the balloon 30. In other words, the distal end of the inner shaft 11, which is also the distal end of the balloon catheter 100 itself, protrudes to the distal end side from the distal end of the outer tube 10A located inside the balloon 30. To be exact, the distal end of the balloon catheter 100 is configured by the distal end tip 333 attached to the distal end portion of the inner shaft 11. When the axial length of the distal end tip 333 is large, the distal end of the inner shaft 11 may terminate inside the balloon 30.

The balloon 30 includes an intermediate portion 31 expandable in a cylindrical shape by the expansion fluid supplied from the fluid supply/discharge port 22, a distal end portion 33 attached to the shaft 10 (the inner shaft 11) on the distal end side with respect to the intermediate portion 31, and a proximal end portion 35 attached to the shaft 10 on the proximal end side with respect to the intermediate portion 31. The intermediate portion 31 is a portion that axially couples the distal end portion 33 and the proximal end portion 35 attached to the shaft 10, and is also hereinafter referred to as a straight portion 31. The distal end portion 33 of the balloon 30 includes a distal end side neck portion 331 attached to the shaft 10 (the inner shaft 11 or the distal end tip 333 described later) at the distal end side, and a distal end side tapered portion 332 (hereinafter also referred to as a distal end side cone portion 332) formed in a tapered shape or a truncated cone shape from the distal end of the straight portion 31 toward the distal end side neck portion 331. The proximal end portion 35 of the balloon 30 includes a proximal end side neck portion 351 attached to the outer periphery of the outer tube 10A of the shaft 10 at the proximal end side, and a proximal end side tapered portion 352 (hereinafter also referred to as a proximal end side cone portion 352) formed in a tapered shape or a truncated cone shape from the proximal end of the straight portion 31 toward the proximal end side neck portion 351.

Figure 2:
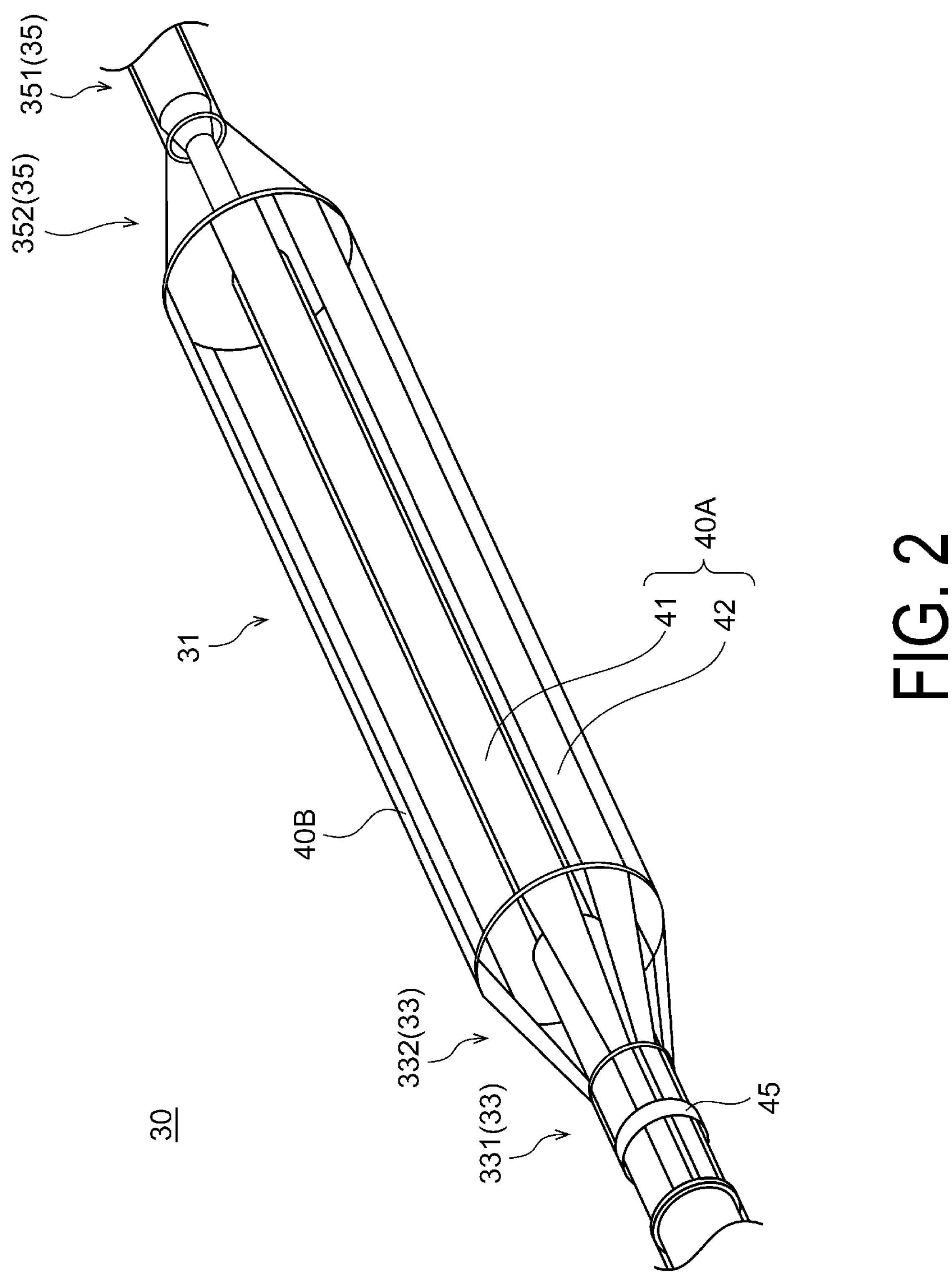
FIG. 2 is a perspective view illustrating a balloon during expansion.
Figure 3:
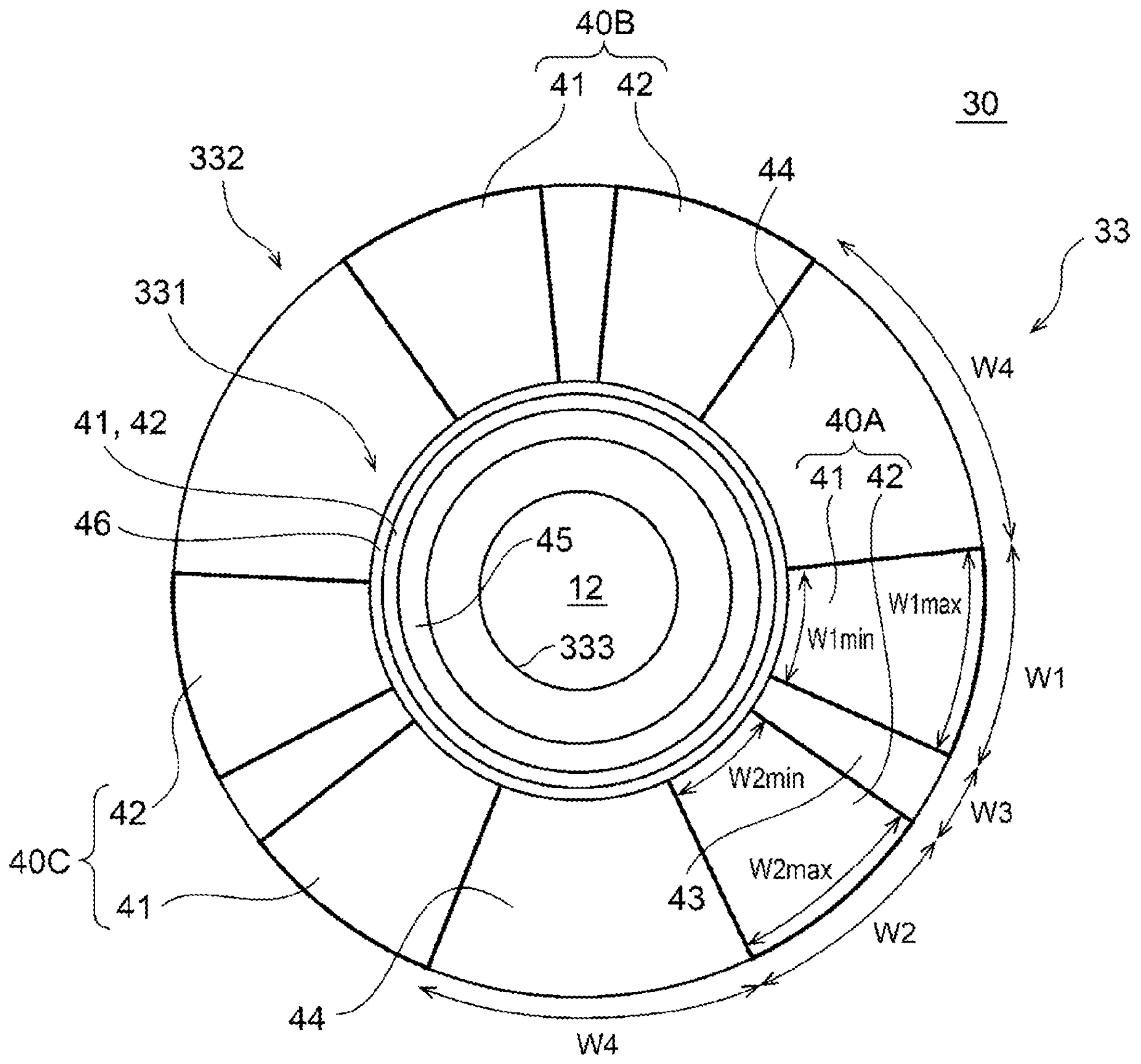
FIG. 3 is a front view illustrating a distal end portion of the balloon during expansion.

FIG. 2 is a perspective view illustrating the balloon 30 during expansion, and FIG. 3 is a front view illustrating the distal end portion 33 of the balloon 30 during expansion. A plurality of electrode pairs 40 are formed on the surfaces of the distal end portion 33 and the straight portion 31 of the balloon 30 along the axial direction from the distal end side toward the proximal end side. Note that the electrode pair 40 may be formed on the surface of the proximal end portion 35 of the balloon 30. In the example of FIGS. 2 and 3, three electrode pairs 40A, 40B, 40C are disposed at substantially equal intervals along the circumferential direction in FIG. 3. Hereinafter, the electrode pairs 40A, 40B, 40C are collectively referred to as the electrode pair 40 except that each of the electrode pairs 40A, 40B, 40C needs to be distinguished.

The electrode pair 40 includes a pair of band-shaped electrodes 41, 42 formed on the surfaces of the distal end portion 33 and the straight portion 31 of the balloon 30. Each of the band-shaped electrodes 41, 42 is a thin film electrode formed in a band shape along the axial direction from the distal end side toward the proximal end side. The band-shaped electrodes 41, 42 are circumferentially separated by an electrode clearance 43 over the respective entire lengths. Note that the band-shaped electrodes 41, 42 may be connected without a clearance in the circumferential direction in at least the distal end side of the distal end side cone portion 332 and/or the distal end side neck portion 331. To improve foldability of the balloon 30, which will be described later, the width of the electrode clearance 43 in the circumferential direction is preferably equal to or greater than the thickness of the balloon 30 (for example, 20 μm). A circumferential width W1 of the band-shaped electrode 41 and a circumferential width W2 of the band-shaped electrode 42 are substantially equal to one another, and are greater than a circumferential width W3 of the electrode clearance 43 therebetween. Note that the width W1 of the band-shaped electrode 41 and the width W2 of the band-shaped electrode 42 may be different from one another. In that case, the width W3 of the electrode clearance 43 is smaller than both of the width W1 of the band-shaped electrode 41 and the width W2 of the band-shaped electrode 42 between which the electrode clearance 43 is interposed (that is, W3<W1 and W3<W2). Also, the width W1 of the band-shaped electrode 41, the width W2 of the band-shaped electrode 42, and the width W3 of the electrode clearance 43 in each of the electrode pairs 40A, 40B, 40C may be substantially equal to one another or may be different from one another. Note that each of the widths W1, W2, W3, and a width W4 and widths of an interpolation electrode 47 and clearances 481, 482 described later needs not to be constant along the axial direction, and only needs to satisfy a relationship described in the present embodiment in any cross-sectional surface perpendicular to the axial direction.

To improve the foldability of the balloon 30 described later, the width W1, W2 of each of the band-shaped electrodes 41, 42 in the distal end portion 33 (and/or the proximal end portion 35) is smaller than the width W1, W2 of each of the band-shaped electrodes 41, 42 in the intermediate portion 31. Specifically, as illustrated in FIG. 3, the width W1 of the band-shaped electrode 41 decreases from a maximum width W1max in the straight portion 31 to a minimum width W1min in the distal end side neck portion 331 in the distal end side cone portion 332. Similarly, the width W2 of the band-shaped electrode 42 decreases from a maximum width W2max in the straight portion 31 to a minimum width W2min in the distal end side neck portion 331 in the distal end side cone portion 332. Also, the width W3 of the electrode clearance 43 decreases from a maximum width in the straight portion 31 to a minimum width in the distal end side neck portion 331 in the distal end side cone portion 332. Note that in the straight portion 31, the widths W1, W2 (and the width W3 of the electrode clearance 43) of the band-shaped electrodes 41, 42 are substantially constant at the maximum widths W1max, W2max, respectively, and in the distal end side neck portion 331, the widths W1, W2 (and the width W3 of the electrode clearance 43) of the band-shaped electrodes 41, 42 are substantially constant at minimum widths W1min, W2min, respectively.

The electrode pairs 40A, 40B, 40C are circumferentially separated by the electrode pair clearances 44 over the respective entire lengths. Note that the respective electrode pairs 40A, 40B, 40C may be connected without clearances in the circumferential direction in at least the distal end side of the distal end side cone portion 332 and/or the distal end side neck portion 331. The circumferential width W4 of each electrode pair clearance 44 is greater than the width W3 of the electrode clearance 43 in each of the electrode pairs 40. Also, typically, as illustrated in FIG. 3, the circumferential width W4 of each of the electrode pair clearances 44 is greater than the widths W1, W2 of the band-shaped electrodes 41, 42 in each of the electrode pairs 40. However, when the widths W1, W2 of the band-shaped electrodes 41, 42 increase, such as a case of increasing the expansion diameter of the balloon 30, the widths W1, W2 are greater than the width W4 of each of the electrode pair clearances 44 in some cases. Note that the widths W4 of the three electrode pair clearances 44 in FIG. 3 may be substantially equal to one another, or may be different from one another. That is, the three electrode pairs 40A, 40B, 40C may be disposed at substantially equal intervals, or may be disposed at different intervals in the circumferential direction on the surface of the balloon 30.

Figure 4:
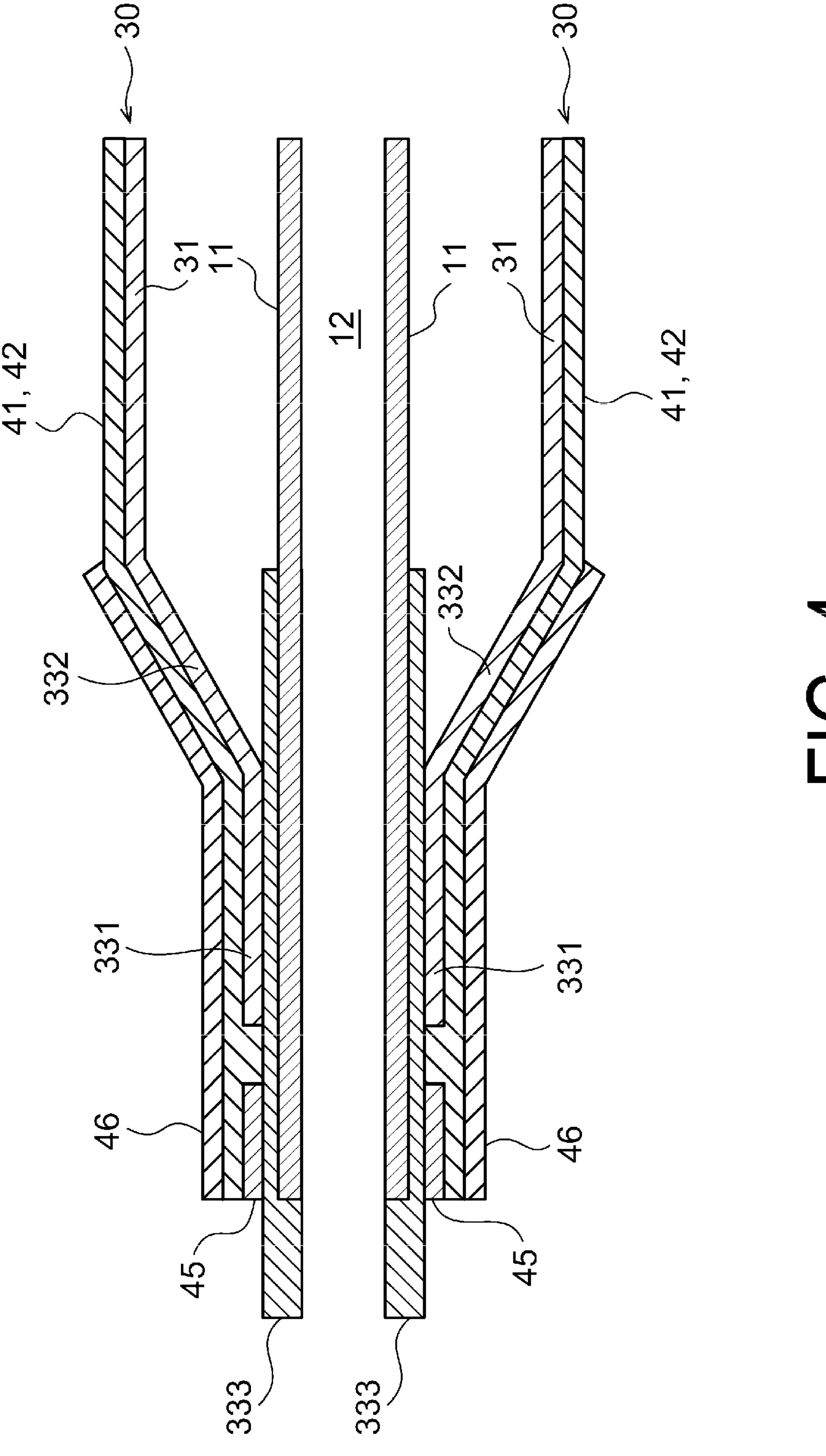
FIG. 4 is a cross-sectional view of the balloon during expansion.

With reference to FIG. 4, which is a cross-sectional view of the balloon 30 during expansion, the configuration of the distal end portion 33 of the balloon 30 will be described. A wire lumen 12 into which the guidewire is insertable with the guidewire port 23 is formed inside the inner shaft 11, which penetrates the inside of the balloon 30 in the axial direction. The outer diameter of the inner shaft 11 is, for example, 1.4 mm, and the inner diameter of the inner shaft 11 (the outer diameter of the wire lumen 12) is, for example, 1.1 mm. The substantially cylindrical distal end tip 333 (a portion of the shaft 10) that covers and protects the inner shaft 11 including its outer periphery is provided at the distal end portion of the inner shaft 11. The outer diameter of the distal end tip 333 is, for example, 2.0 mm, and the inner diameter of the distal end tip 333 is same as the inner shaft 11 and is, for example, 1.1 mm. The distal end tip 333 is formed by, for example, a hard resin. The guidewire passing through the wire lumen 12 can be extended from the inner shaft 11 and the open end of the distal end tip 333 to outside the balloon catheter 100.

The distal end side neck portion 331 of the balloon 30 is attached to the proximal end side of the outer periphery of the distal end tip 333. Additionally, an annular ring electrode 45 as a peripheral electrode is provided on the distal end side of the outer periphery of the distal end tip 333. The outer diameter of the ring electrode 45 is, for example, 2.22 mm, and the inner diameter of the ring electrode 45 is, for example, 2.08 mm. The band-shaped electrode 41, 42, such as a silver (Ag), which fills this gap, is formed to approximately 20 μm in thickness on the outer peripheries of the ring electrode 45 and the balloon 30 by, for example, printing. Note that the ring electrode 45 may be provided on the outer peripheries of the band-shaped electrode 41, 42 formed previously. The distal ends of the band-shaped electrodes 41, 42 are substantially matched with the distal end of the ring electrode 45, and are at the position retracted toward the proximal end side from the distal end of the distal end tip 333. In other words, the distal end tip 333 projects to the distal end side with respect to the band-shaped electrodes 41, 42 and the ring electrode 45. This makes it possible to prevent damage to the band-shaped electrodes 41, 42 and the ring electrode 45 even in a case where the distal end of the distal end tip 333 is brought into contact with an inner wall of a sheath (not illustrated), which guides the balloon 30 to the treatment site while storing the balloon 30, and a body tissue.

An insulating coating 46 having a thickness between 10 μm and 20 μm is provided on the outer peripheries of the band-shaped electrodes 41, 42 from the distal end to the distal end side neck portion 331 and the distal end side cone portion 332. In this manner, the band-shaped electrodes 41, 42 allow applying a high frequency to the treatment site at the outer periphery or the side surface of the straight portion 31 having the stable expansion shape (cylindrical shape). Furthermore, the ring electrode 45 connects the plurality of band-shaped electrodes 41, 42 in the circumferential direction at the distal end portion 33 of the balloon 30. Specifically, as illustrated in FIG. 3, the ring electrode 45 electrically connects the six band-shaped electrodes 41, 42. Thus, the six band-shaped electrodes 41, 42 can apply a high frequency at substantially the same voltage and current to the treatment site. Accordingly, even when the balloon 30 inserted into the body rotates in the circumferential direction, the high frequency can be reliably applied to the treatment site. Note that, although not illustrated, the conductive wire passing through the electrical cable 26, the handle portion 20, the shaft 10, and the inside of the balloon 30 (the inner shaft 11) from the electrical connector 21 is connected to any of the ring electrode 45 and/or the band-shaped electrodes 41, 42 at the distal end portion of the balloon catheter 100. Thus, the electrical connector 21 connected to a high-frequency power supply (not illustrated) can apply a high frequency to the band-shaped electrodes 41, 42 on the surface of the balloon 30.

Figure 5:
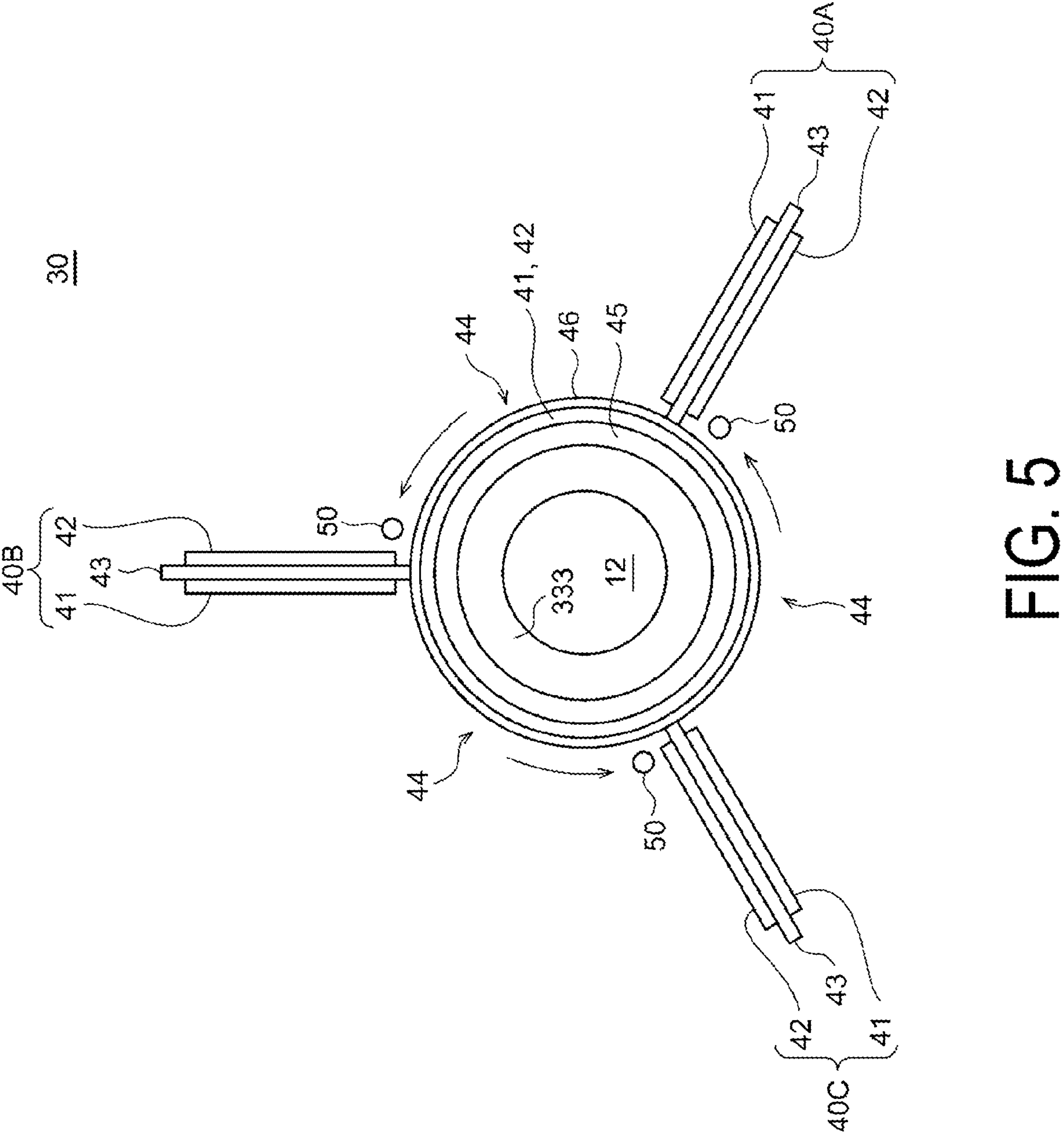
FIG. 5 schematically illustrates the folded balloon.

The balloon 30 as described above is folded before expansion. FIG. 5 schematically illustrates the folded balloon 30 (the expanded balloon 30 is as in FIG. 3). In each of the electrode pairs 40A, 40B, 40C, a fold (peak) of the balloon 30 is formed at the electrode clearance 43, which separates the band-shaped electrodes 41, 42 in the circumferential direction. Additionally, folds (valleys) of the balloon 30 are formed at both end portions of the electrode pair clearance 44, which separates the respective electrode pairs 40A, 40B, 40C in the circumferential direction. On the other hand, in each of the band-shaped electrodes 41, 42, the fold of the balloon 30 is not formed. Thus, in the present embodiment, since the foldability of the balloon 30 is improved by the electrode clearance 43 in each of the electrode pairs 40A, 40B, 40C and the electrode pair clearance 44 between the respective electrode pairs 40A, 40B, 40C, the possibility of formation of the fold of the balloon 30 on the band-shaped electrodes 41, 42 decreases. Accordingly, a change in a conduction aspect of the high frequency in the folded band-shaped electrodes 41, 42, and eventually instability of a treatment by the balloon catheter 100 can be effectively prevented.

As described above, the folded balloon 30 has the folded shape constituted by a plurality of folding unit structures. The folding unit structure is formed of the fold (peak) and the two folds (valleys) on both sides in the circumferential direction of the peak. In the three folding unit structures in FIG. 5, the balloon 30 is folded such that the fold (peak) is formed at the electrode clearance 43 and the folds (valleys) are formed at the electrode pair clearances 44. In other words, the balloon 30 is folded such that these folds (peaks/valleys) are formed so as to avoid the band-shaped electrodes 41, 42.

Figure 6:
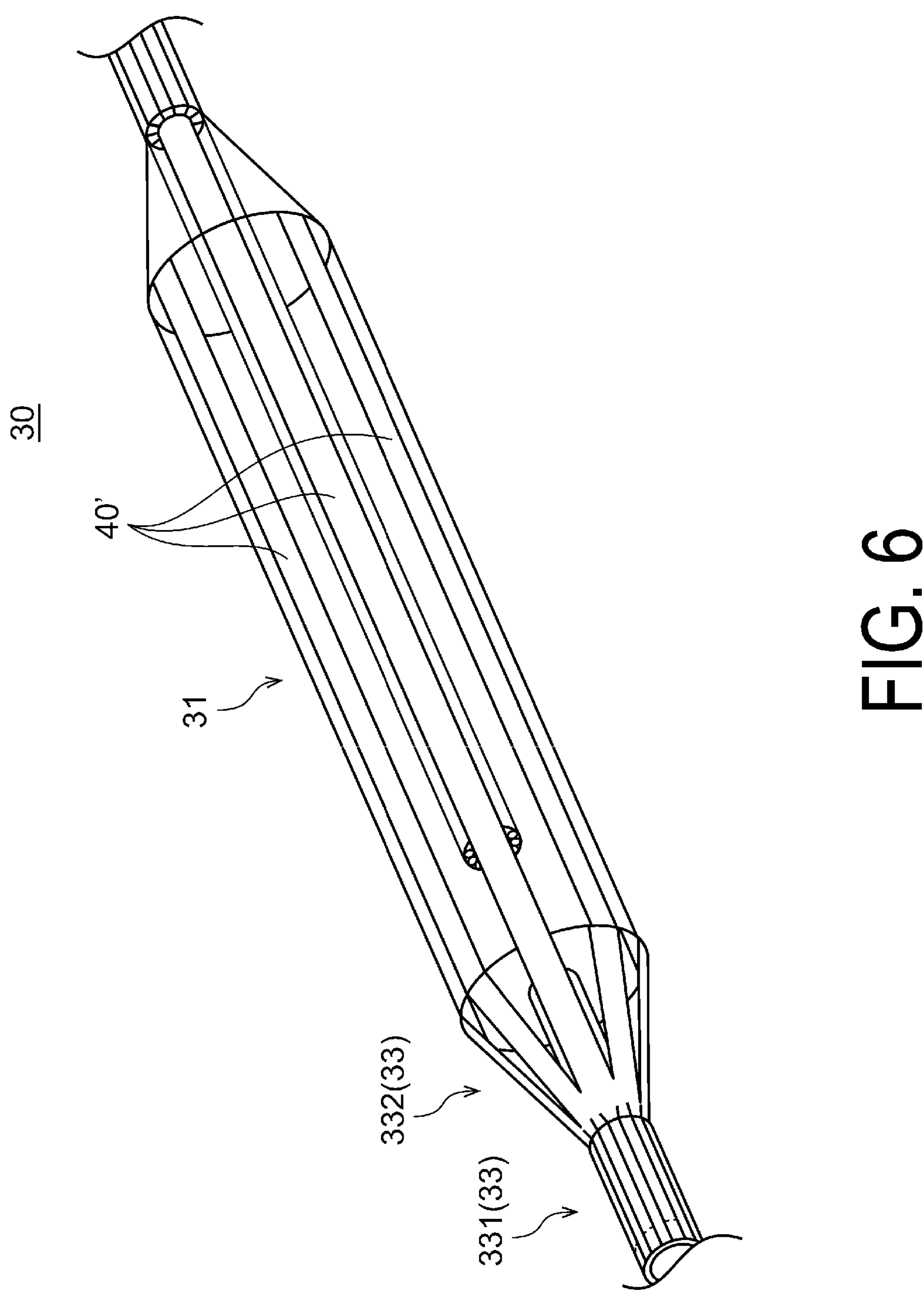
FIG. 6 is a perspective view of a balloon according to a comparative example.
Figure 7:
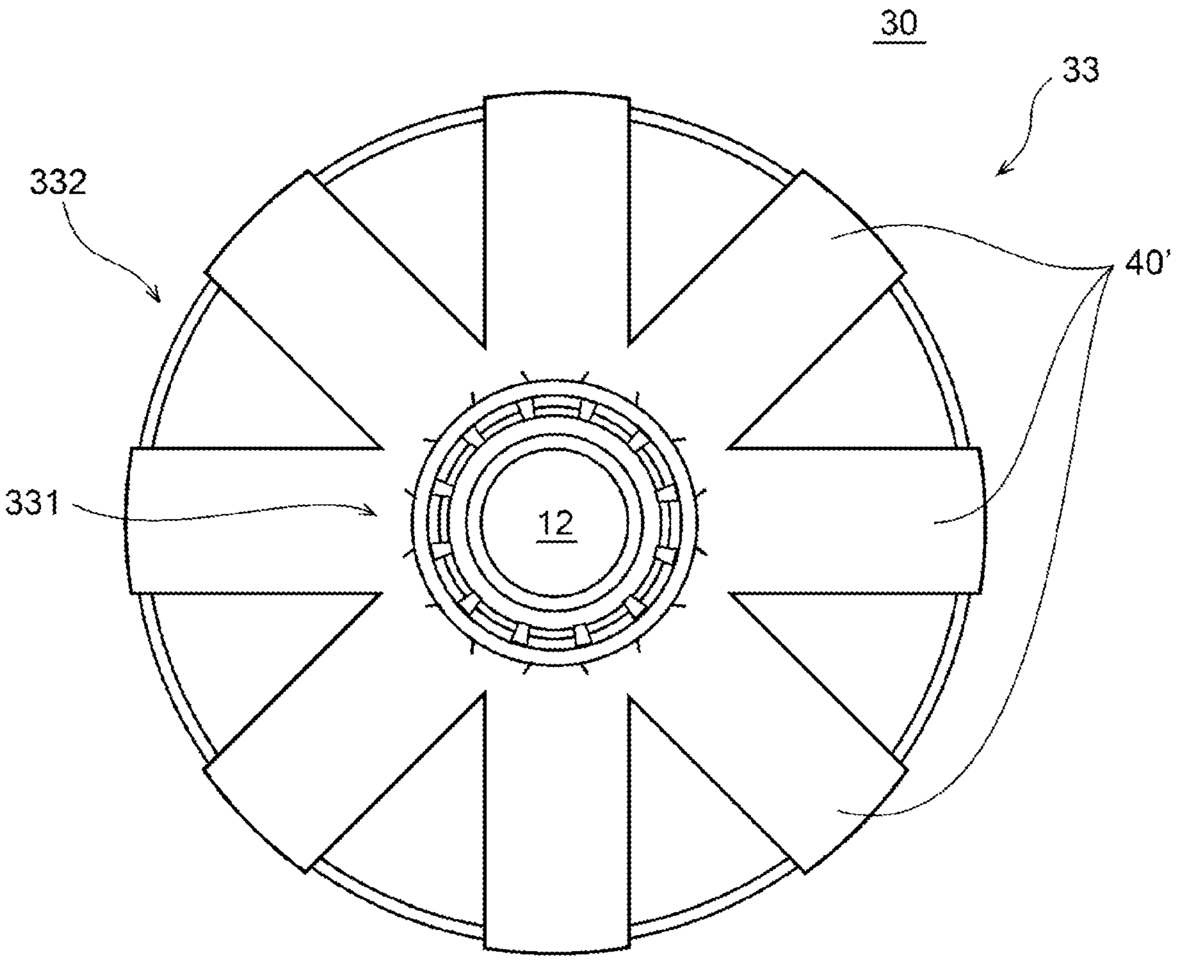
FIG. 7 is a front view of the balloon according to the comparative example.

FIG. 6 illustrates a perspective view of the balloon 30 of a comparative example (corresponding to FIG. 2 of the present embodiment), and FIG. 7 illustrates a front view of the balloon 30 of the comparative example (corresponding to FIG. 3 of the present embodiment). As illustrated in FIG. 6, a plurality of band-shaped electrodes 40' are formed at equal intervals in the circumferential direction along the axial direction from the distal end side toward the proximal end side on the surfaces of the distal end portion 33 and the straight portion 31 of the balloon 30. Also, as illustrated in FIG. 7, a width in the circumferential direction of each of the band-shaped electrode 40' is constant from the straight portion 31 to the distal end portion 33. Thus, the respective band-shaped electrodes 40' are merged into one on the distal end side cone portion 332.

The balloon 30 according to the comparative example cannot be folded as illustrated in FIG. 5 of the present embodiment. Specifically, unlike FIG. 5, the possibility of formation of the folds of the balloon 30 on the respective band-shaped electrodes 40' is extremely high. In particular, since the respective band-shaped electrodes 40' are merged into one on the distal end side cone portion 332, a fold is inevitably formed when the balloon 30 is folded. In contrast, in the present embodiment of FIG. 3, since the respective band-shaped electrodes 41, 42 are separated by the electrode clearances 43 or the electrode pair clearances 44 even on the distal end side cone portion 332, formation of the folds on the respective band-shaped electrodes 41, 42 can be prevented. As described above, according to the present embodiment, the possibility that the folds are formed on the band-shaped electrodes 41, 42 is significantly reduced compared to that in the comparative example, and instability of the treatment by the balloon catheter 100 due to the folded band-shaped electrodes 41, 42 can be effectively prevented.

Note that the balloon 30 before use is wrapped in a folded state further from the state of FIG. 5. As schematically illustrated in FIG. 5, each of the electrode pairs 40A, 40B, 40C folded with the electrode clearance 43 as the fold (peak) is pressed from the lateral side by a wrapping pin 50 that rotates in the circumferential direction to wrap it around the outer periphery of the shaft 10 (the inner shaft 11) (the balloon 30 or each of the electrode pairs 40A, 40B, 40C may be rotated in the circumferential direction with respect to the still wrapping pin 50). The balloon 30 with a wrapping cover attached from the outer periphery in this state is stored until being used. The balloon 30 with the wrapping cover removed immediately prior to use reaches the treatment site through the guidewire while stored in a sheath (not illustrated). Then, the balloon 30 extending or exposed from the distal end of the sheath expands by the expansion fluid and applies a high frequency to the treatment site by the band-shaped electrodes 41, 42 on the surface of the balloon 30. At this time, the balloon 30 folded so as not to form a fold on the plurality of band-shaped electrodes 41, 42, which are formed on of the surface of the balloon 30 along the axial direction from the proximal end side toward the distal end side, expands by the expansion fluid. In addition, by regulating the flow of the expansion fluid inside the balloon 30 by a flow regulating portion, such as a valve, the inside of the balloon 30 is maintained at a predetermined pressure suited for the ablation treatment by the band-shaped electrodes 41, 42. That is, the ablation treatment by the band-shaped electrodes 41, 42 is performed while the flow regulating portion maintains the expanded state of the balloon 30. The balloon 30 after the end of ablation treatment contracts by the discharge of the expansion fluid, is again stored in the sheath, and is decannulated to outside the body with the sheath.

The respective electrode pairs 40A, 40B, 40C are formed by, for example, screen printing on the surface of the balloon 30 in the expanded state as in FIG. 3. Although the respective electrode pairs 40A, 40B, 40C can be formed while the balloon 30 contracted as in FIG. 5 is folded in advance, the folds almost disappear by heat during calcination of the respective electrode pairs 40A, 40B, 40C. Therefore, folding the balloon 30 in advance before calcination of the respective electrode pairs 40A, 40B, 40C does not have much meaning. It is efficient that after the respective electrode pairs 40A, 40B, 40C are formed on the surface of the balloon 30 in the expanded state as in FIG. 3, the balloon 30 is folded and wrapped in accordance with the arrangement of the respective electrode pairs 40A, 40B, 40C, electrode clearances 43, and electrode pair clearances 44 as in FIG. 5. Note that, since each of the electrode pairs 40A, 40B, 40C is the thin film, it cannot be expected that the fold as in FIG. 5 is naturally formed by simply contracting the balloon 30. Therefore, it is preferable to perform a fold forming step and a wrapping step in accordance with the arrangement of the respective electrode pairs 40A, 40B, 40C, electrode clearances 43, and electrode pair clearances 44 as in FIG. 5.

Figure 8:
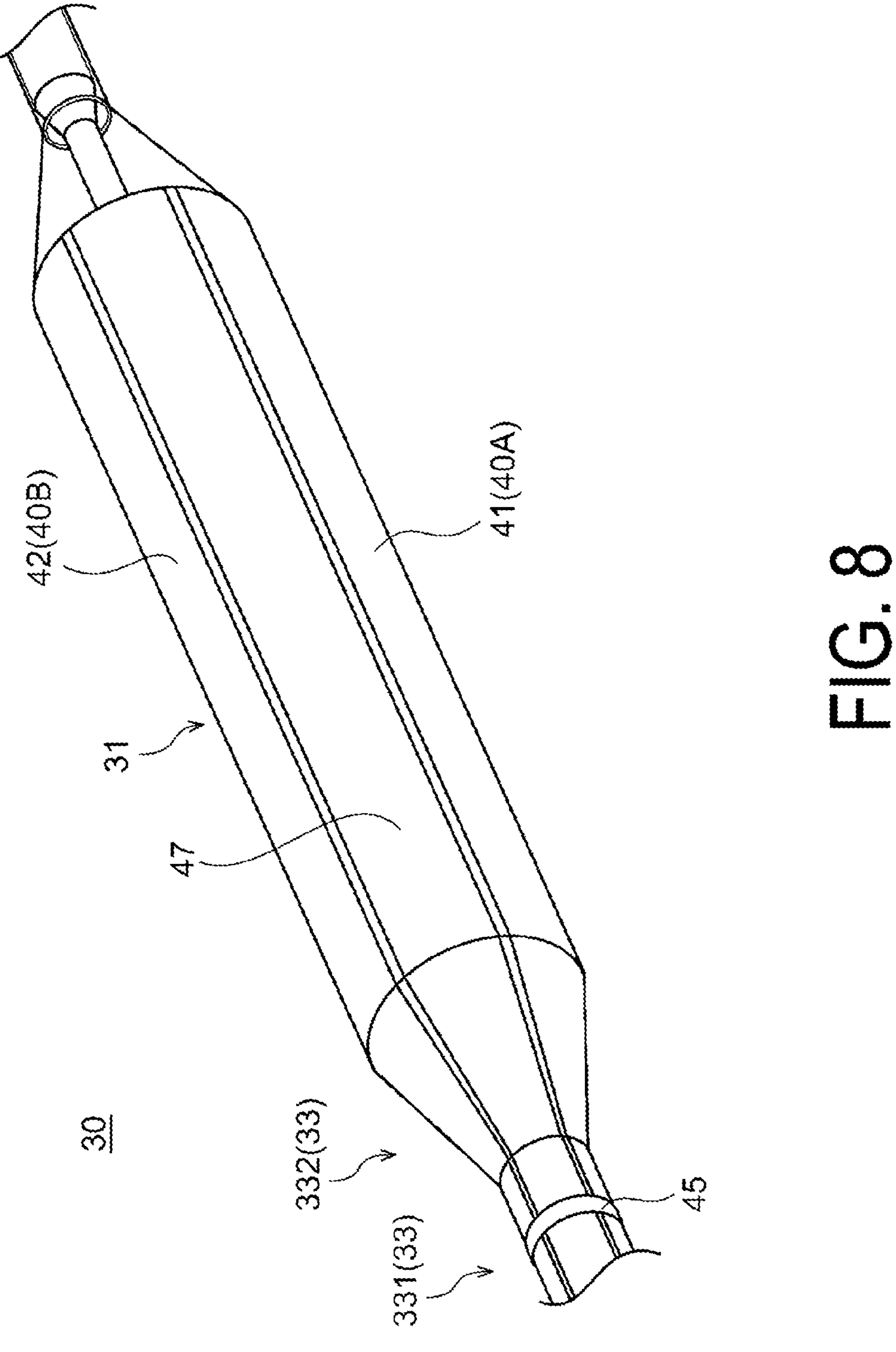
FIG. 8 is a perspective view of a balloon (during expansion) according to a modification.
Figure 9:
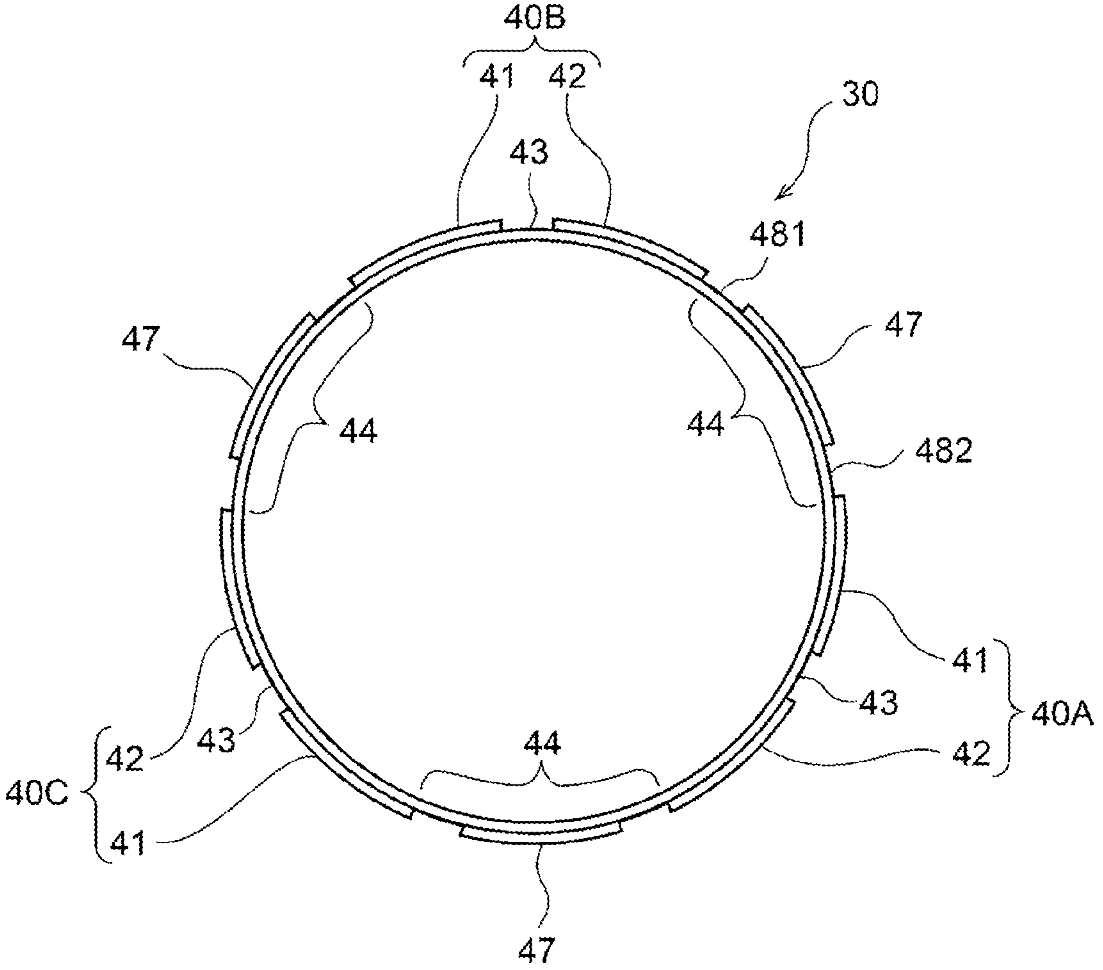
FIG. 9 is a simplified front view of the balloon (during expansion) according to the modification.
Figure 10:
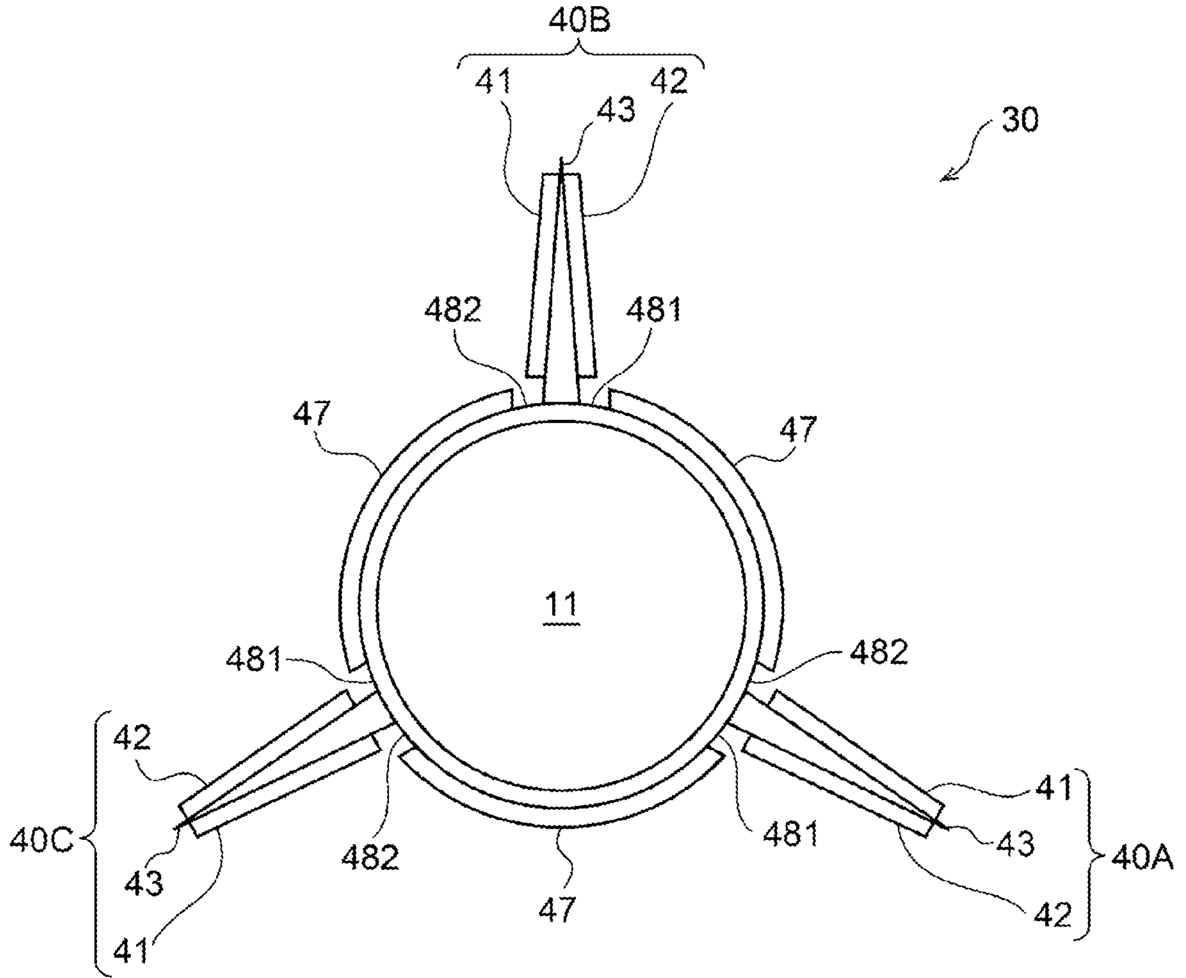
FIG. 10 is a simplified front view of the balloon (during folding) according to the modification.

Next, a modification of the balloon 30 will be described. FIG. 8 is a perspective view (corresponding to FIG. 2) of the balloon 30 (during expansion) according to the modification, FIG. 9 is a simplified front view (corresponding to FIG. 3) of the balloon 30 (during expansion) according to the modification, and FIG. 10 is a simplified front view (corresponding to FIG. 5) of the balloon 30 (during folding) according to the modification. In the present modification, as illustrated in FIG. 9, the band-like interpolation electrodes 47 are formed in the electrode pair clearances 44 between the respective electrode pairs 40A, 40B, 40C. Similarly to the band-shaped electrodes 41, 42 in the respective electrode pairs 40A, 40B, 40C, the interpolation electrodes 47 are electrodes of thin films formed along the axial direction on the surfaces of the distal end portion 33 and the straight portion 31 of the balloon 30. As illustrated in FIG. 10, the plurality of interpolation electrodes 47 are disposed intermittently along the outer periphery of the inner shaft 11 during folding the balloon 30. Accordingly, the sum of the widths of the plurality of interpolation electrodes 47 is smaller than the circumference (the outer periphery) of the inner shaft 11.

The respective interpolation electrodes 47 are circumferentially separated by the respective electrode pairs 40A, 40B, 40C and clearances 481, 482 adjacent to both sides across the respective entire lengths. Note that the respective interpolation electrodes 47 may be connected to the respective electrode pairs 40A, 40B, 40C without clearances in the circumferential direction in at least the distal end side of the distal end side cone portion 332 and/or the distal end side neck portion 331. Similarly to the electrode clearance 43, the width in the circumferential direction of the clearances 481, 482 is preferably equal to or greater than the thickness (e.g., 20 μm) of the balloon 30. Additionally, similarly to the band-shaped electrodes 41, 42 in each of the electrode pairs 40A, 40B, 40C, each of the interpolation electrodes 47 has the width at the distal end portion 33 smaller than the width at the intermediate portion 31 to improve the foldability of the balloon 30.

As illustrated in FIG. 8, the respective interpolation electrodes 47 are electrically connected to the band-shaped electrodes 41, 42 in each of the electrode pairs 40A, 40B, 40C by the ring electrode 45, which is provided at the distal end portion of the balloon catheter 100. Thus, the six band-shaped electrodes 41, 42 and the three interpolation electrodes 47 can apply a high frequency at substantially the same voltage and current to the treatment site. According to the present modification, a high frequency can be applied to a wider area of the treatment site than the embodiment of FIGS. 2 and 3.

The balloon 30 of the present modification is folded as in FIG. 10. In each of the electrode pairs 40A, 40B, 40C, the fold (peak) of the balloon 30 is formed in the electrode clearance 43 separating the band-shaped electrodes 41, 42 in the circumferential direction. Additionally, the folds (valleys) of the balloon 30 are formed in the clearances 481, 482 separating the respective interpolation electrodes 47 and the respective electrode pairs 40A, 40B, 40C in the circumferential direction. On the other hand, each of the band-shaped electrodes 41, 42 or each of the interpolation electrodes 47 does not have a fold of the balloon 30. In this manner, in the present modification, since foldability of the balloon 30 is improved by the electrode clearance 43 in each of the electrode pairs 40A, 40B, 40C and the clearances 481, 482 between the respective interpolation electrodes 47 and the respective electrode pairs 40A, 40B, 40C, a possibility of formation of a fold of the balloon 30 on the band-shaped electrodes 41, 42 and the interpolation electrode 47 decreases. Accordingly, a change in a conduction aspect of the high frequency in the folded band-shaped electrodes 41, 42 and interpolation electrode 47, and eventually instability of a treatment by the balloon catheter 100 can be effectively prevented.

As described above, the folded balloon 30 has the folded shape constituted by a plurality of folding unit structures. The folding unit structure is formed of the fold (peak) and the two folds (valleys) on both sides in the circumferential direction of the peak. In the three folding unit structures in FIG. 10, the balloon 30 is folded such that the fold (peak) is formed at the electrode clearance 43 and the folds (valleys) are formed at the clearances 481, 482. In other words, the balloon 30 is folded such that these folds (peaks/valleys) are formed so as to avoid the band-shaped electrodes 41, 42 and the interpolation electrode 47.

The present disclosure has been described above based on the embodiments. It should be understood by those skilled in the art that the embodiments are examples, that various modifications are possible in the combination of components and processing operations, and that such modifications are also within the scope of the present disclosure.

REFERENCE SIGNS LIST

10 Shaft
11 Inner shaft
21 Electric connector
22 Fluid supply/discharge port
30 Balloon
31 Intermediate portion
33 Distal end portion
35 Proximal end portion
40 Electrode pair
41 Band-shaped electrode
42 Band-shaped electrode
43 Electrode clearance
44 Electrode pair clearance
45 Ring electrode
47 Interpolation electrode
100 Balloon catheter
481 Clearance
482 Clearance

The invention claimed is:

1. A balloon catheter, comprising:

a shaft to be inserted into a body;

a balloon attached to a distal end side of the shaft and expandable by a fluid supplied from a proximal end side of the shaft;

an electrode pair formed on a surface of the balloon along an axial direction from the proximal end side toward the distal end side, widths in a circumferential direction of respective electrodes being greater than a width of an electrode clearance that separates the respective electrodes in the circumferential direction in the electrode pair; and a peripheral electrode that directly contacts the respective electrodes in the circumferential direction in at least any of a distal end portion where the balloon is attached to the shaft and a proximal end portion;

wherein a plurality of the electrode pairs are formed on the surface of the balloon, and a width of an electrode pair clearance that separates the respective electrode pairs in the circumferential direction is greater than the width of the electrode clearance, wherein the each electrode is a band-shaped electrode, and wherein the length of the band-shaped electrode along the axial direction is larger than the width of the band-shaped electrode along the circumferential direction.

2. The balloon catheter according to claim 1, wherein the balloon before expansion is folded, and a fold of the balloon is formed in each of the electrode clearances.

3. The balloon catheter according to claim 1, wherein the balloon before expansion is folded, and a fold of the balloon is formed in the electrode pair clearance.

4. The balloon catheter according to claim 1, wherein the balloon before expansion is folded, and a fold of the balloon is not formed in each of the electrodes.

5. The balloon catheter according to claim 1, further comprising an interpolation electrode formed along the axial direction in the electrode pair clearance.

6. The balloon catheter according to claim 5, wherein the balloon before expansion is folded, and a fold of the balloon is formed in a clearance that separates the interpolation electrode and each of the electrode pairs in the circumferential direction.

7. The balloon catheter according to claim 1, wherein the balloon includes both end portions attached to the shaft and an intermediate portion that couples both the end portions in the axial direction, and wherein a width of each of the electrodes in at least any of end portions among both the end portions decreases in a direction from the intermediate portion toward the end portion.

8. A method of actuating the balloon catheter according to claim 1, comprising:

expanding the balloon that is attached to the distal end side of the shaft and folded such that a fold is not formed on the plurality of electrodes formed along the axial direction from the proximal end side toward the distal end side on the surface of the balloon by the fluid.

* * * * *